US006966316B2

(12) United States Patent
Lowry

(10) Patent No.: US 6,966,316 B2
(45) Date of Patent: Nov. 22, 2005

(54) CLEAN GAS PURGE FOR BREATHING GAS REGULATOR

(75) Inventor: Philip L. Lowry, Placentia, CA (US)

(73) Assignee: Survivair Respirators, Inc., Santa Ana, CA (US)

( * ) Notice: Subject to any disclaimer, the term of this patent is extended or adjusted under 35 U.S.C. 154(b) by 186 days.

(21) Appl. No.: 10/322,833

(22) Filed: Dec. 18, 2002

(65) Prior Publication Data

US 2004/0000311 A1 Jan. 1, 2004

Related U.S. Application Data

(60) Provisional application No. 60/390,964, filed on Jun. 24, 2002.

(51) Int. Cl.[7] .......................... A61M 16/00; A62B 9/02

(52) U.S. Cl. .......................... 128/204.26; 128/205.24; 137/908

(58) Field of Search ...................... 128/200.24, 205.24, 128/204.26, 201.22, 201.24, 201.28, 206.15, 128/207.12, 204.25, 205.22, 207.16, 201.27, 128/204.18, 205.11; 137/414, 484.2, 494, 137/908

(56) References Cited

U.S. PATENT DOCUMENTS 3,216,416 A * 11/1965 Mitchell ................ 128/204.26
3,716,053 A * 2/1973 Almovist et al. ...... 128/201.15
5,357,950 A 10/1994 Wippler
5,464,009 A * 11/1995 Tatarek-Gintowt ..... 128/205.24
5,787,882 A * 8/1998 Hamilton ............... 128/204.26
5,970,977 A * 10/1999 Sattelberg .............. 128/205.24
6,091,331 A 7/2000 Toft
6,651,662 B2 * 11/2003 Prete et al. ............ 128/206.21
6,718,976 B1 * 4/2004 Matsuoka .............. 128/204.26
6,729,331 B2 * 5/2004 Kay ...................... 128/205.24
2004/0149286 A1 * 8/2004 Haston .................. 128/204.26

* cited by examiner

*Primary Examiner*—Teena Mitchell

(74) *Attorney, Agent, or Firm*—Knobbe, Martens, Olson & Bear, LLP

(57) ABSTRACT

A self contained breathing apparatus (SCBA) served by a source of breathing gas with a mask and a demand regulator connected to the mask. The regulator has a flexible diaphragmatic member having a side exposed to ambient that moves in response to pressure differentials to cause a valve mechanism to introduce breathing gas to the mask. A passage provides breathing gas over said diaphragm exposed to ambient which can be a passage from one side of the diaphragm to the other. A protective cover can overlie the passage which can be displaced upon gas flow through the passage. The method purges ambient contaminants from the diaphragm by providing breathing gas over the diaphragm through an opening of the diaphragm.

17 Claims, 8 Drawing Sheets

CLEAN GAS PURGE FOR BREATHING GAS REGULATOR

This application claims the benefit and priority of U.S. Provisional Application Ser. No. 60/390,964; filed Jun. 24, 2002; entitled a Clean Air Purge For Breathing Apparatus Regulator; Applicant: Philip L. Lowry.

BACKGROUND OF THE INVENTION

1. Field of the Invention

The field of this invention is within the art of breathing gas regulators. It pertains to those breathing gas regulators that are often referred to as demand or second stage regulators that regulate an intermediate pressure that can be used by a party breathing from a self contained breathing apparatus. More particularly, the invention incorporates a second stage regulator having a diaphragm which can be made in part of an elastomeric material which flexes inwardly and outwardly upon a user's breathing.

2. Description of the Prior Art

The prior art of self contained breathing apparatus (SCBA's) relies upon a source of breathing gas such as a pressurized tank of air. The pressurized tank is connected to a first stage or high pressure regulator to regulate the high pressure. From the first stage regulator, a connection is made to a second stage or demand regulator.

The second stage regulator is such wherein a user can breath the breathing gas from the second stage or demand regulator upon inhalation. Such second stage regulators are often used in conjunction with masks for purposes of providing breathing gas under pressure free from contaminants.

As can be appreciated, self contained breathing apparatus is often used in fire and rescue work as well as in industrial environments where certain atmospheres can be deleterious to a user.

The use of such fire, rescue and industrial self contained breathing apparatus is such where it is often exposed to contaminated gases that can attack certain portions of a regulator over an extended period of time. Such contaminated gases and contaminants can be in the form of those gases that are currently known with regard to chemical warfare. Also, certain deleterious gases and contaminants can be generated from industrial fires, explosions, and other conditions. Such chemical contaminants can affect a user of self contained breathing apparatus such as a fireman or an industrial clean-up worker.

Another problem with regard to self contained breathing apparatus in severe environments where contaminants are being used pertains to those gases in chemical warfare. One of these gases is known as Sarin gas. Also, chemical, biological, radiological and nuclear contaminants can affect a mask adversely. This is particularly true when the mask and the breathing apparatus relies upon an elastomeric diaphragm in order to effect the demand regulator functions as is known in the prior art.

Contaminants such as Sarin gas and other deleterious substances can affect the diaphragms adversely. The diaphragms are often times made of an elastomeric material, whether it be silicone rubber or other types of elastomerics which are subject to deterioration when exposed to such gases and contaminants.

Elastomers generally have a matrix which can create interstices in adverse environments when contaminants are exposed to the surface of such elastomers. In effect, the contaminants disperse into the rubber and are then eventually transmitted to the other side to one degree or the other.

It has been found that such contaminants can permeate the diaphragm of a demand regulator within thirty (30) minutes. However, with the use of this invention, it has substantially extended that period of time.

Self contained breathing apparatus is usually under positive pressure within the mask and in the regulator area in order to exclude any contaminants from seeping into the mask. By maintaining a positive pressure within the mask above ambient or atmospheric pressure, the seal around a user's face and the other areas can exclude contaminants and other deleterious gases. As can be understood, a simple contaminant such as smoke, if leaked into the mask, could cause a severe problem for a fireman or industrial worker.

It has been found that when a positive pressure is such where the air within the exposed portion of the regulator diaphragm is constantly changed, that it will substantially exclude contaminants from coming into the regulator.

An SCBA regulator has a diaphragm which is exposed to atmosphere and flexes upon inhalation. Exposure to the ambient conditions is such where deleterious gases and contaminants can reach the surface of the elastomeric diaphragm. When these gases and contaminants are substantially eliminated, it has been found that a degree of longevity can be encountered with the diaphragm lasting longer. This invention is directed toward increasing the longevity through breathing gas being exposed to and substantially displacing deleterious gases and contaminants from the diaphragm of an SCBA demand regulator.

SUMMARY OF THE INVENTION

In summation, this invention comprises a self contained breathing apparatus (SCBA) having a demand regulator with a diaphragm that flexes and moves upon pressure differentials such as inhalation, and is exposed to ambient conditions through an opening, and has an improved positive flow of fresh non-contaminated breathing gas over the surface thereof for protecting the elastomer of the diaphragm.

More particularly, the invention comprises an SCBA having a source of breathing gas such as a tank of air. The breathing gas is regulated by a high pressure or first stage regulator to an intermediate pressure. The regulated intermediate pressure gas is conducted to a second stage or demand regulator.

The second stage or demand regulator is emplaced within a mask having a lens and skirt for sealing the mask to a user's face. Within the demand regulator is a diaphragm which moves in response to a user's inhalation, exhalation, or other pressure differential, movements. The diaphragm is connected to a valve apparatus which opens and closes the valve apparatus conducting intermediate pressure to a user.

The diaphragm is exposed to ambient atmospheric conditions so that any contaminants or deleterious gases can affect the outer surface. In order to cleanse the outer surface of deleterious gases or contaminants a constant delivery of gas is disposed across the face thereof. The delivery of the gas helps to remove deleterious gases and contaminants to limit attack by the contaminants. This serves to preserve the elastomer of the diaphragm for an extended period of time.

DETAILED DESCRIPTION OF THE PREFERRED EMBODIMENTS

Figure 1:
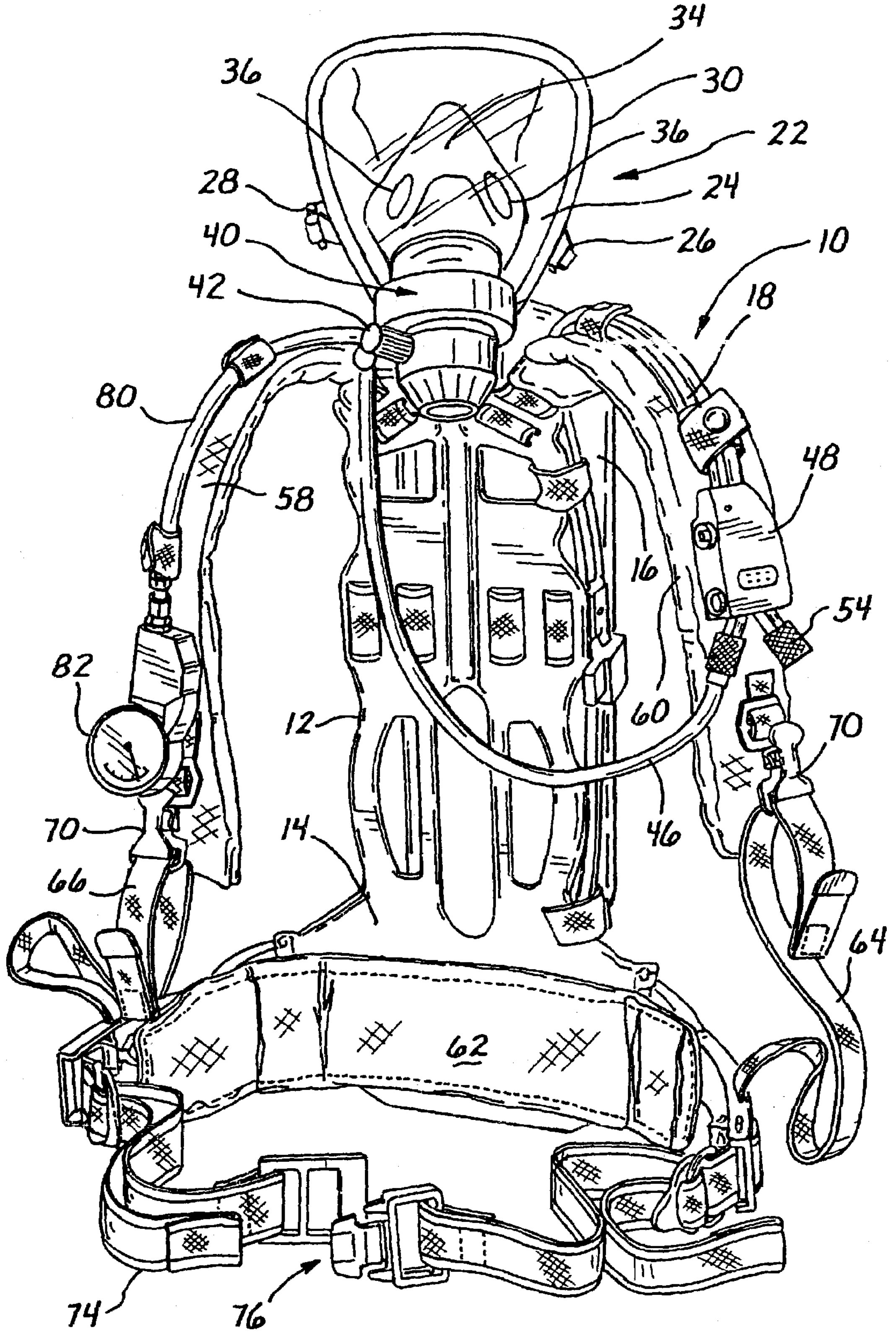
FIG. 1 shows a perspective view of the self contained breathing apparatus of this invention.

Looking more specifically at FIG. 1 it can be seen that a self contained breathing apparatus (SCBA) 10 has been shown. The self contained breathing apparatus 10 incorporates a backpack 12. The backpack 12 generally is of an inverted T shaped configuration having a cross member 14 thereof.

The backpack 12 has straps in the back in order to carry a tank 16 of breathing gas. The tank 16 of breathing gas is fluidly connected by means of a high pressure regulator and a valve which is not shown in the back. The high pressure regulator regulates gas to an intermediate pressure hose or conduit 18.

In order to provide a user with a protective environment, a mask 22 is provided having a lens 24. A pair of strap attachments 26 and 28 are shown which secure the mask to a user's face. The frame of the mask 22 is in the form of a metal or other stiff frame 30 to which the structure of the lens 24 and the straps 26 and 28 are connected.

Interiorly of the mask 22 is an oral nasal mask 34. The oral nasal mask 34 has gas delivered thereinto through valves 36 on either side. The gas is exposed to the lens 24 which helps to clear the mask of moisture and condensation. A user can breath through the valve 36 from air supplied through a second stage regulator.

A second stage or demand regulator 40 is shown. The second stage or demand regulator 40 has a bypass valve operably attached to a knob 42. The bypass valve attached to the knob 42 allows for air to be delivered directly to the mask 22 without the regulator functions.

In order to deliver breathing gas to the second stage regulator 40, the intermediate pressure passes from the hose 18 through an extension of the hose 46. The extension of the hose 46 is interconnected and passes through a personal alarm safety system 48 which indicates to a user when pressure is low or in the alternative it indicates to other people when a user is in a condition wherein he or she requires emergency help. To this extent, the personal alarm safety system is incorporated in this application by reference to U.S. Pat. No. 6,091,331 entitled an Emergency Worker and Fireman's Dual Emergency Warning System issued Jul. 18, 2000 naming Carl Toft; David Haston; Carl Schaefer; and, Duane Becker as inventors, commonly owned herewith.

A quick disconnect bypass valve 54 is shown which allows a second party to receive gas from the breathing gas source in case the second party's apparatus fails.

In order to hold the backpack and the entire self contained breathing apparatus to a user, shoulder straps 58 and 60 are shown. The shoulder straps 58 and 60 are connected to a hip pad 62 having adjustment straps 64 and 66 with alligator clips or adjustments 70 attached to either one.

In order to adjust the self contained breathing apparatus 10, a waist belt 74 is shown having a buckle 76 with a quick disconnect.

A line 80 is connected to the high pressure side of the SCBA and has a pressure gauge 82 connected to it in order to apprise a user of the amount of pressure remaining in the tank.

Figure 2:
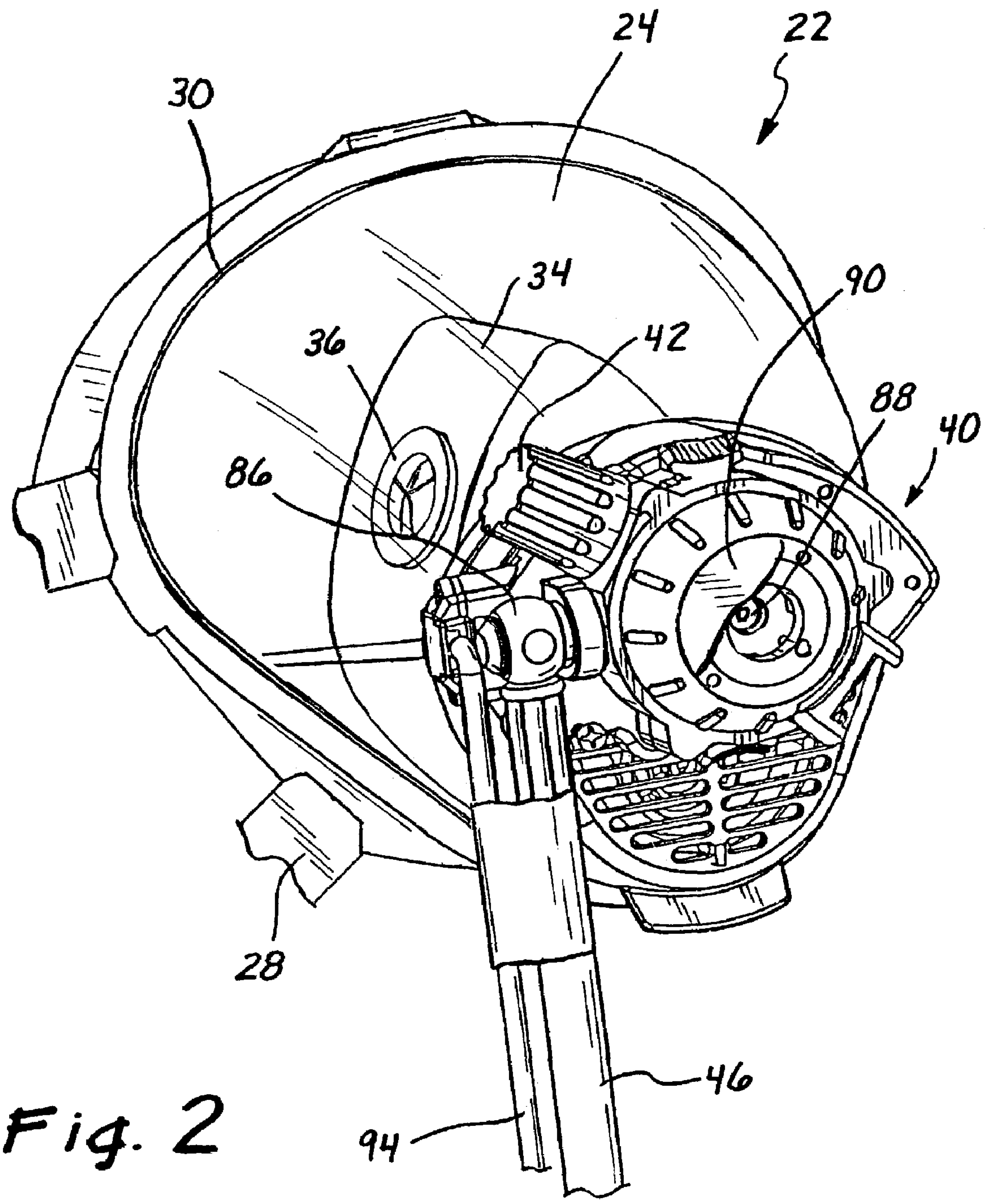
FIG. 2 shows a perspective view of a mask and demand regulator of the self contained breathing apparatus as shown in FIG. 1.

Looking at FIG. 2, the regulator 40 can be shown along with the mask 22 with its attendant lens 24, oral nasal mask 34, and rim 30 which provides a frame. The regulator 40 can be seen attached to the oral nasal mask 34 with a valve 36 on either side. Air delivered into the mask 22 at a positive pressure can be inhaled by a user through the valve 36 into the oral nasal mask.

The demand regulator 40 is served by the intermediate pressure that has been regulated from its high pressure and conducted through a conduit 46 which is connected to a swivel fitting 86. The swivel fitting 86 allows gas to be introduced to the regulator 40 for demand regulation. A purge button 88 is shown with a cover 90 for allowing a user to push the button and provide for the introduction of air into the mask A bypass valve can be turned with a bypass knob 42 connected to a bypass valve to allow gas to be introduced through the regulator 40.

In order to provide for data on a user's display, a connecting line 94 is shown. Signals from a processor or other device connected to a transducer for monitoring tank 16 pressure can provide such items as pressure of the gas in the tank as well as other electrical timing functions to be displayed within the mask 22.

Figure 3:
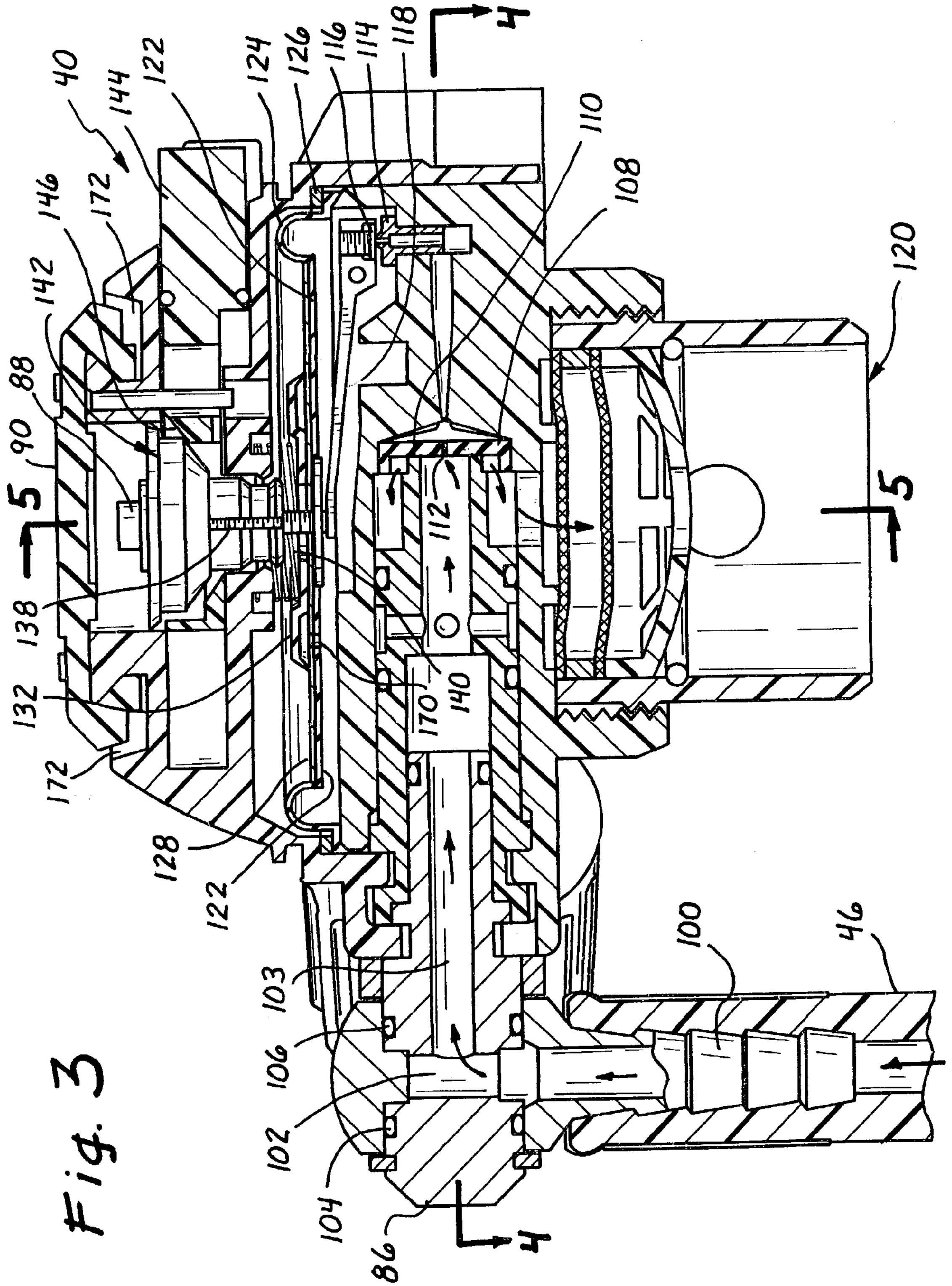
FIG. 3 shows a cross-sectional view through the regulator detailing this invention when the purge orifice is covered.

The swivel connector 86 can be seen in FIG. 3 in a cross-section wherein the hose 46 has been connected thereto by means of a barbed fitting 100. The barbed fitting 100 is seated such that the hose 46 directly connects to a passage 102 sealed by O rings 104 and 106. The breathing gas then travels through a connecting passage 103. The passage 103 terminates at a main valve comprising a valve cover 108 having an orifice 112 seated against a valve seat 110. The valve cover 108 with its orifice 112 is controlled by means of a pilot valve 114.

The pilot valve 114 has a pilot valve cover 116 that is in turn connected to a lever 118. The gas flow upon displacement of the valve cover 108 by actuation of the pilot valve cover 116 being unseated by the lever 118 can be seen in the direction of the small arrows. The flow of gas is indicated by the small arrows around the surrounding circumferential groove or chamber and then passing outwardly toward the mask through a main passage 120.

Constant positive pressure in the mask 22 and regulator can be maintained by the pilot valve 114.

The pilot valve 114 provides for a constant minor flow into the mask 22. Other positive pressure conduits or connections can be utilized for providing positive pressure both into the mask and behind the operating diaphragm to effect this invention. However, in this case the pilot valve is set so that it functions to maintain approximately one and one half inches (water) pressure in the mask 22 and behind the diaphragm 122. In effect, the chamber behind the diaphragm 122 is held at a positive pressure as well as the inside of the mask by the pilot valve lifting when pressure drops below a pre-established pressure. The area of the diaphragm in connected relationship to the lever 118 is referred to herein as the inside surface or portion of the diaphragm. The opposite ambient exposed surface of diaphragm 122 is referred to as the outside.

The regulator 40 functions by means of the diaphragm 122 supported at either end by a circumferential groove or flange 124 formed by a channel for greater flexural response. The groove, or flange 124 has a terminal point which seats in the regulator behind a ring member 126.

The diaphragm 122 flexes inwardly and outwardly upon pressure changes and differentials in order to cause the lever 118 to function. In effect the pilot valve 114 operates to maintain the positive pressure. The diaphragm 122 is backed by a support plate 128 that is stiffer than the elastomeric diaphragm and can be made of metal or plastic. The support plate 128 allows for sufficient support and stiffening of the diaphragm 122 so that it does not collapse entirely during inhalation and exhalation or other pressure changes.

Figure 6:
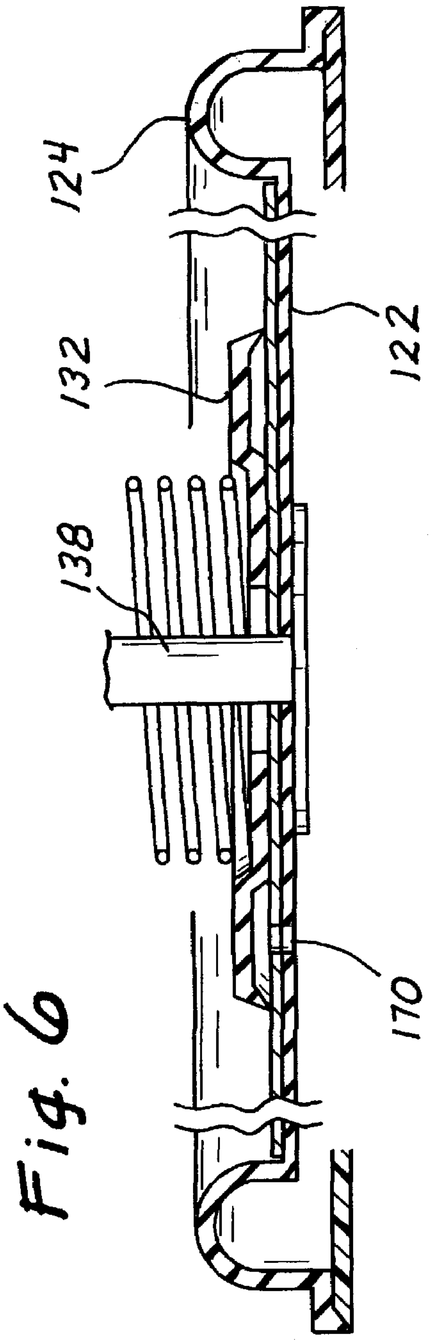
FIG. 6 shows a cross-sectional view of the orifice cover overlying the diaphragm of FIG. 5 when the gas is not flowing Through the purge orifice of the diaphragm.
Figure 7:
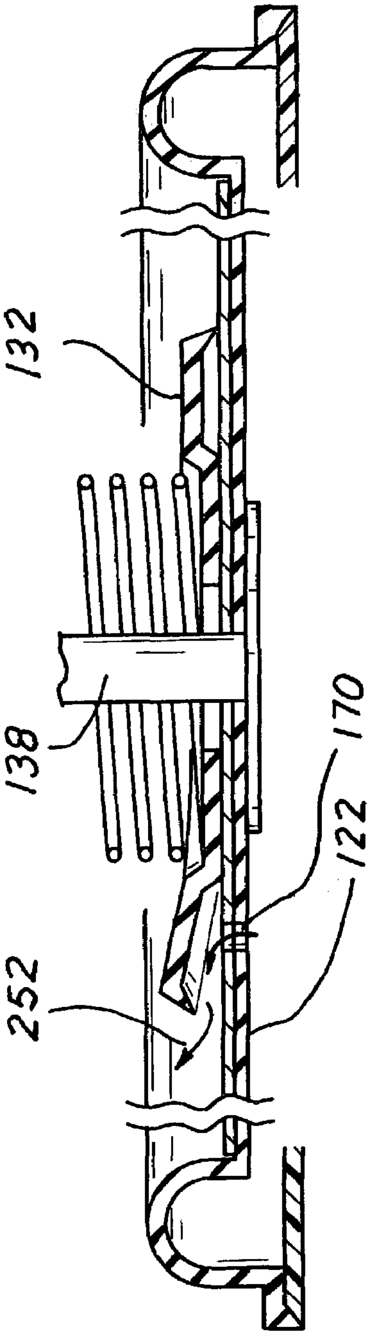
FIG. 7 shows a sectional view of the purge orifice with the air flowing over the diaphragm of FIG. 5.

An air purifying orifice passage, or conduit 170 of this invention is shown having an elastomeric flap, lid, or membrane orifice cover 132. The orifice 170 can be plural in number to cause flow through the diaphragm in multiple locations. These orifice(s) can be randomly located through the diaphragm or placed in a circumferential orientation depending upon the air flow desired. The orifice cover lid or membrane 132 is a circumferential disk like member as seen in FIG. 6 of this invention in a non-displaced mode. In FIG. 7 of this invention it is shown in a displaced mode showing the escape of air or breathing gas. This is detailed hereinafter in a more specific manner.

The diaphragm 122 is connected to a screw member 138 that is spring biased by a coil spring 140 on the outside of the diaphragm interfacing with an inverted cam driven member 142. The inverted cam driven member 142 is driven over detents at one end. This occurs when displacement by a cam driver rod 144 pushes a surface 146 against the member 142 lifting it upwardly by the cam rod 144 overcoming a coil spring 140 and the detents.

When the diaphragm 122 is then pulled in by a breath, it functions to allow for the continued operation of the regulator 40. The operation of the regulator 40 hereof as to its basic features including the cam member 142 with its detents as well as the other functions have been set forth in U.S. Pat. No. 5,357,950 issued Oct. 25, 1994 entitled Breath Actuated Positive Pressure Demand Regulator With Override naming John Wippler and Max L. Kranz inventors. This patent is commonly assigned to the assignee hereof.

As in the prior art, the elastomeric button 90 can flex downwardly to press against the purge or flow button 88 to allow for the flow of air or gas by displacing the pilot valve cover 116.

In order to provide for a substantially less deleterious environment surrounding the diaphragm 122, air or other breathing gas is allowed to flow through an opening orifice or purge conduit 170 which is covered by the elastomeric cover, flap, lid, or membrane 132. Since flow is provided for the positive pressure in the regulator 40 and mask 22 displacement of flap, lid cover, or membrane 132 takes place by flow through the opening 170.

The purging air can then flow outwardly through a space or opening 172 of the regulator body that is in fluid connected relationship thereto. This is seen more particularly in FIG. 5 wherein the flow is in the direction of arrows 180 outwardly to the ambient or atmosphere through openings 181. This occurs when the cover 132 is in its lifted condition with flow through the opening, orifice, or purge conduit 170 of the diaphragm 122.

The cover, lid, or membrane 132 fundamentally overlies the purge orifice 170 to prevent foreign substances or water from entering the regulator 40. It has been found that the cover 132 if sufficient pressure is maintained through the orifice 170, is not required to prevent back flow of contaminants.

The overall volume of the regulator above the diaphragm namely the volume within the space 186 is approximately 25 cubic centimeters (CC) in volume. Since the mask 22 and the regulator 40 when in use are under positive pressure, a flow during normal use from the space 186 through the outlets, vents, or openings 181 allows for approximately 300 CC's of air per minute to pass thereover. This substantially purges the area over the diaphragm 122. The purging action over the diaphragm 122 can be accomplished by various flow orientations such as tangential direct, or indirect. The net result should be substantial removal of contaminants and deleterious gases away from and over the diaphragm 122.

This purge is particularly critical with regard to the circumferential groove or flange 124 which flexes. This area can be more exposed to the deleterious atmospheres and contaminants than the other portion. Although, a certain flow in the amount of CC's of air are diminished upon breathing, the general function still remains the same. In effect, 600 CC's per minute are developed upon exhalation and 300 CC's per minute upon inhalation. Thus, the contaminants in the space 186 are generally purged by the ability to allow for positive pressure of breathing gas to pass through opening or orifice 170 regardless of the lid, membrane, or disk cover 132 and then outwardly through the spaces or openings 181.

Figure 5:
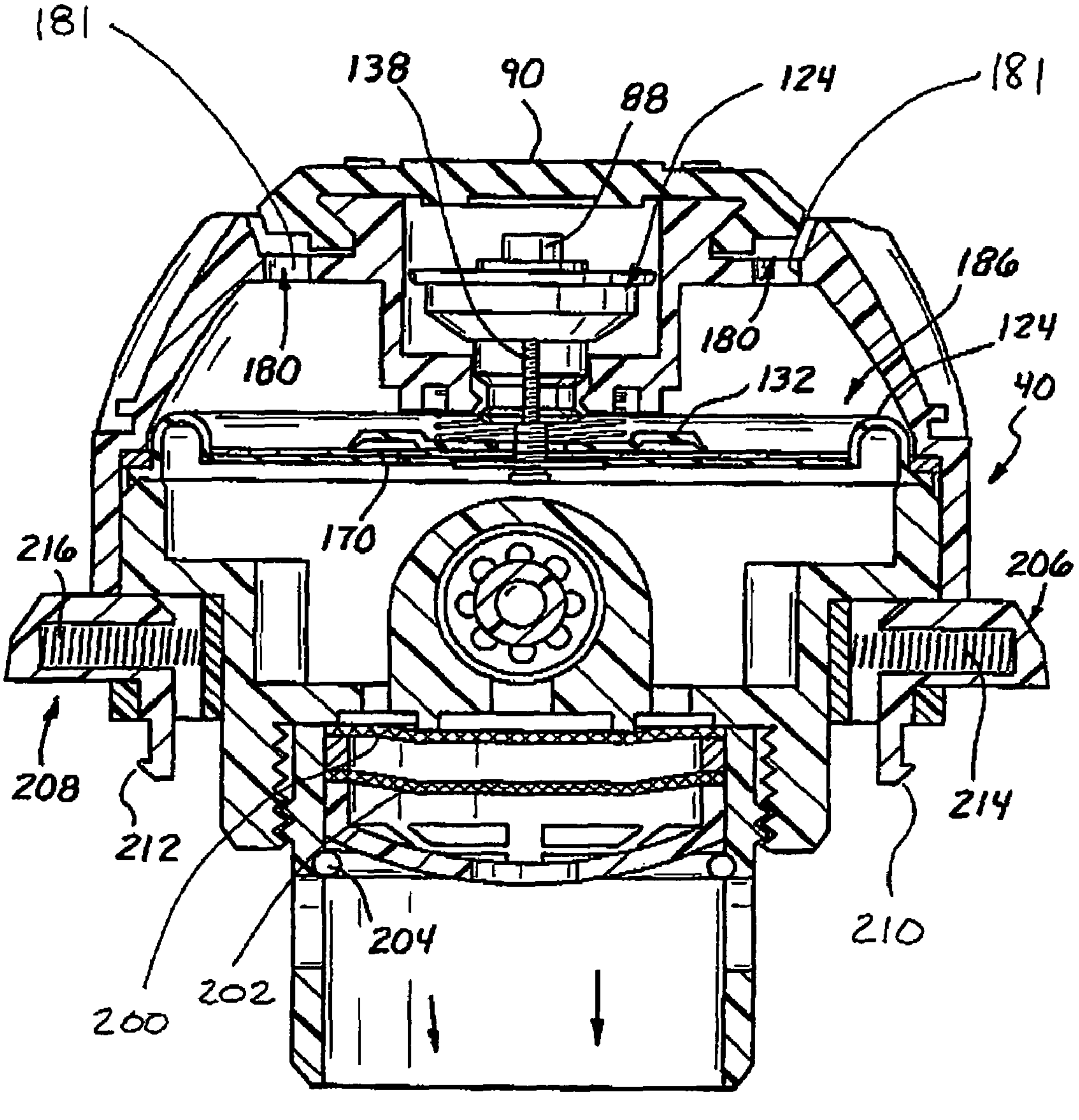
FIG. 5 shows a sectional view substantially rotated ninety degrees from that shown in FIG. 3 along a different sectional view illustrating the purge orifice with air flowing therethrough.

Again, looking more specifically at FIG. 5 it can be seen that the breathing gas is delivered through the regulator 40 to the mask 22 by means of an interconnecting port or main passage 120. This is in the direction of the arrows indicated in the port or main passage 120.

Flow through the port 120 is preceded by a pair of screens 200 and 202. These screens are respectively held in place by means of a circular ring 204.

In order to attach the regulator 40 to the mask 22, a pair of spring loaded latches 206 and 208 are provided. The spring loaded latches 206 and 208 have spring biased connecting latches 210 and 212 respectively biased by springs 214 and 216. In this manner, they are allowed to engage an interior lip, ridge, flange, or other mating configuration of the mask. This enables the regulator 40 to be attached and disconnected from the mask 22 at a user's discretion.

Figure 4:
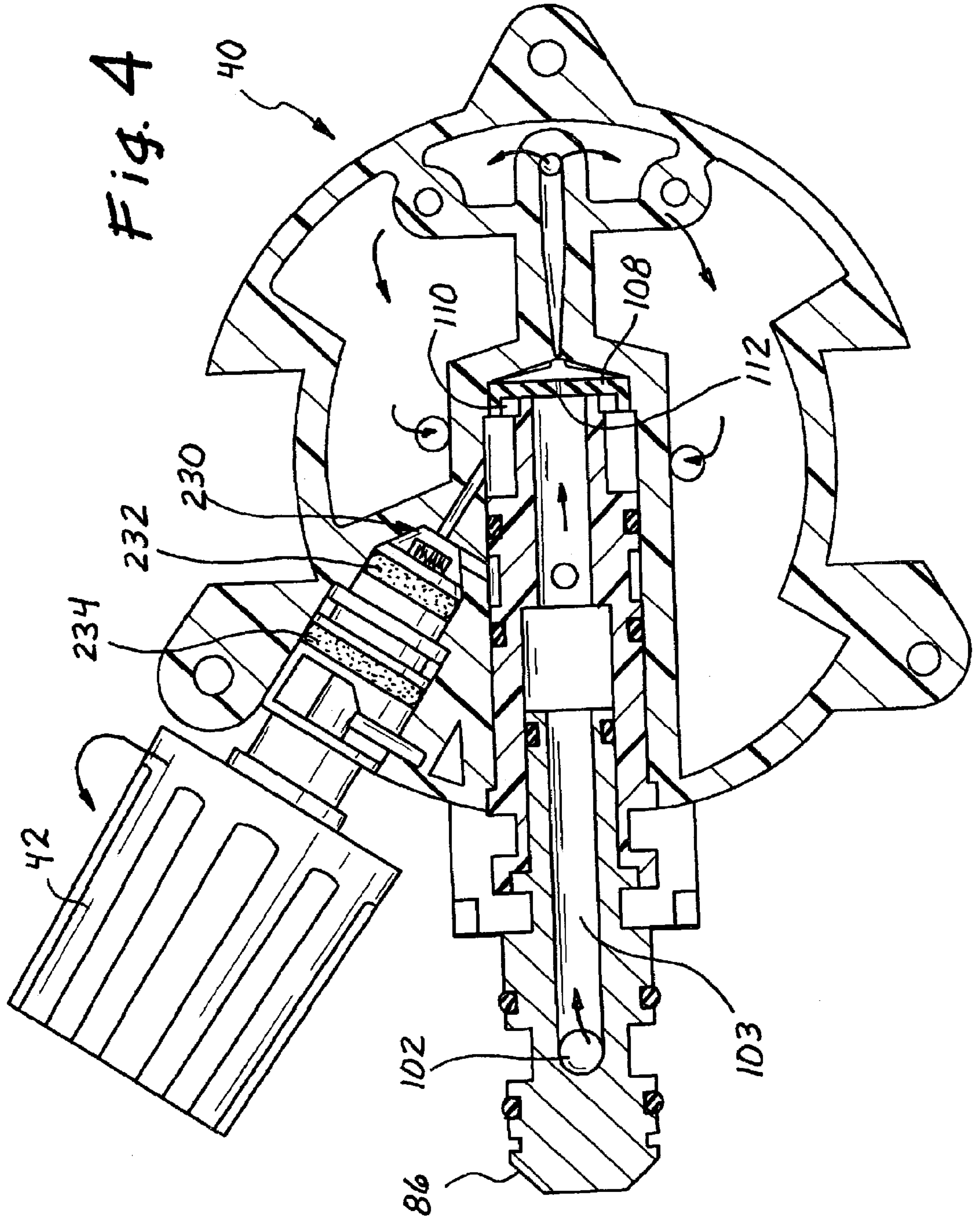
FIG. 4 shows a sectional view along lines 4—4 through the midline area of the regulator shown in FIG. 3.

FIG. 4 shows a midline view in the direction of lines 4—4 of FIG. 3. It specifically details the bypass valve action when the knob 42 is turned. In particular, the bypass valve has a seat 230 which allows the passage of air through the regulator 40 directly into the mask 22 for a user. It is sealed by two O ring seals 232 and 234 so that when it is turned the breathing gas will not substantially slip by the interfaces thereof.

Looking more specifically at FIGS. 6 and 7, it can be seen that the operation of the flap, lid cover, or membrane 132 is shown in its closed position in FIG. 6 and in its opened or flowing condition in FIG. 7.

In FIG. 6, it is seen that the threaded stem member 138 is shown with the spring. The showing is such wherein the breathing gas is not passing through the opening or orifice 170 of the diaphragm. In FIG. 6, there is no gas passing through the opening 170 with the protective flap, cover, or membrane lying across the opening. However, as can be seen in FIG. 7 the gas is passing through the opening 170 against the cover 132 thereby lifting it up. The gas will then pass out thereunder by lifting the cover 132 upwardly and allowing it to pass in the direction of arrow 252.

The foregoing action causes a removal of deleterious contaminants on the surface of the diaphragm 122. The constant flow of air at approximately 300 CC's per minute purges the volume in the chamber 186 since it only constitutes 25 CC's. This serves to eliminate contaminants and deleterious gases over the surface of the diaphragm 122. This helps to substantially diminish the breakdown of the diaphragm beyond the normal half hour limitation when such contaminants such as Sarin gas are exposed to the diaphragm 122.

Figure 8:
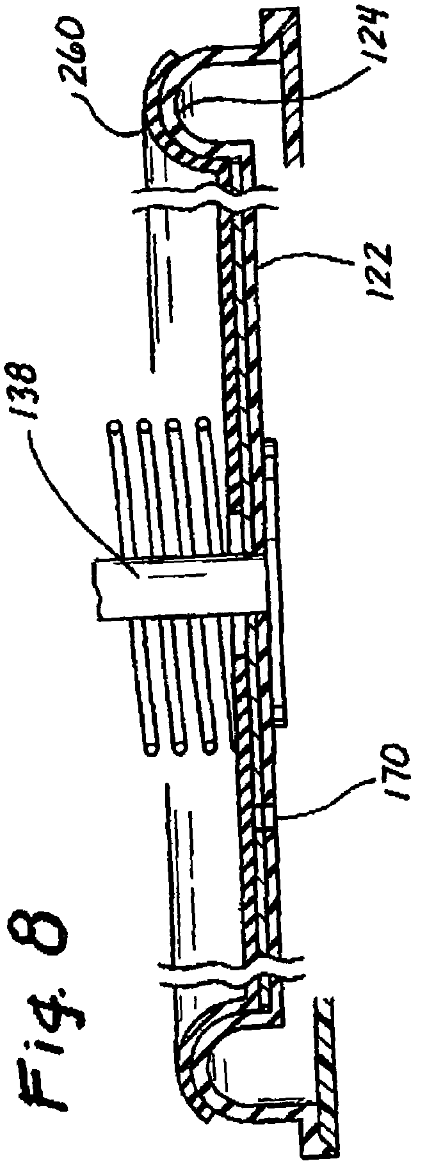
FIG. 8 shows a sectional view of an alternative embodiment of this invention wherein a shroud, or elastomeric cover member forms a membrane overlying a large portion of the diaphragm in order to protect it.
Figure 9:
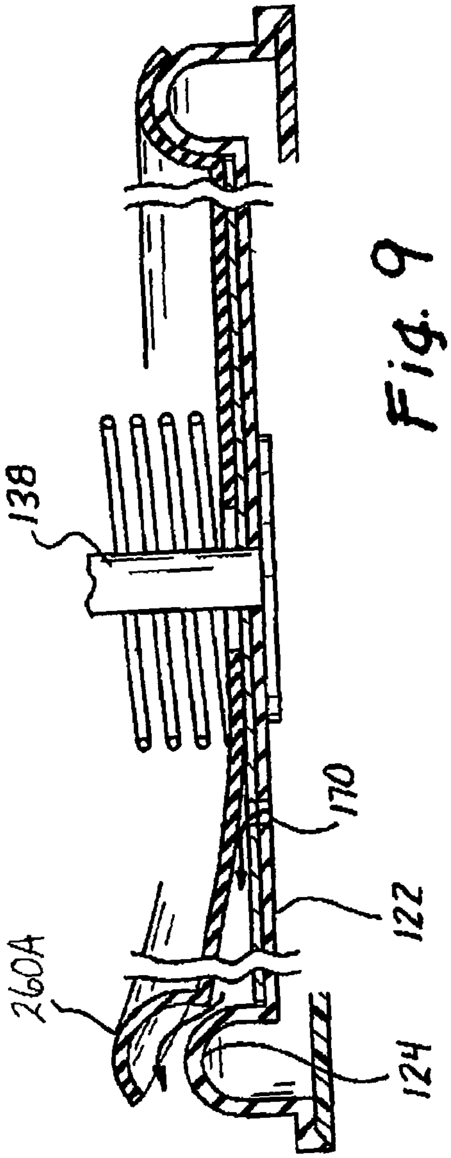
FIG. 9 shows a sectional view of the shroud, or elastomeric cover member covering the diaphragm but in the open position with the air flowing from the orifice.

Looking more particularly at FIG. 8 it can be seen that the diaphragm 122 has been shown with an overlying cover, membrane, or shroud 260 that overlaps the circumferential flanges or channels 124. This overlying cover or shroud 260 allows for the flow of breathing gas through an opening or circumferentially spaced openings 170 to flow over the major surface of the diaphragm 122. With the constant flow of air or breathing gas under the shroud 260, it tends to lift the shroud or cover 260 upwardly so that it can be displaced in the manner of the dotted configuration of the showing of 260A.

The major portion of the diaphragm 122 is covered. Flow through opening 170 then appropriately lifts the cover 260 by the flow of air or breathing gas thereunder through the orifice or opening(s) 170. This allows air to wash and extend over the surface of the major portion or entire diaphragm 122 and be such where it substantially reduces the contaminants on the surface of the diaphragm. All things being considered, the further extension of the cover or shroud 260 over the diaphragm 122 can serve as a more complete protection for the diaphragm in some cases.

It has been found that the protection of the diaphragm 122 can also be effected by merely the flow of air or breathing gas through the orifice(s) 170 that generally washes over or above the diaphragm 122. In such cases if the displacement of contaminants and deleterious gases is sufficient, the requirement of a cover 132 might not be necessary. The requisite is to remove contaminants and deleterious gases from the space 186 on the outside of the diaphragm 122.

It should be understood that any orifice 170 or group of orifices providing purging gas over and on the outside of the diaphragm 122 of sufficient flow will protect the diaphragm. Also, if the flow is sufficient through the purge orifice(s) it will not allow back pressure of contaminants into the mask 22. In such cases the cover only serves a foreign substance protective function.

Figure 10:
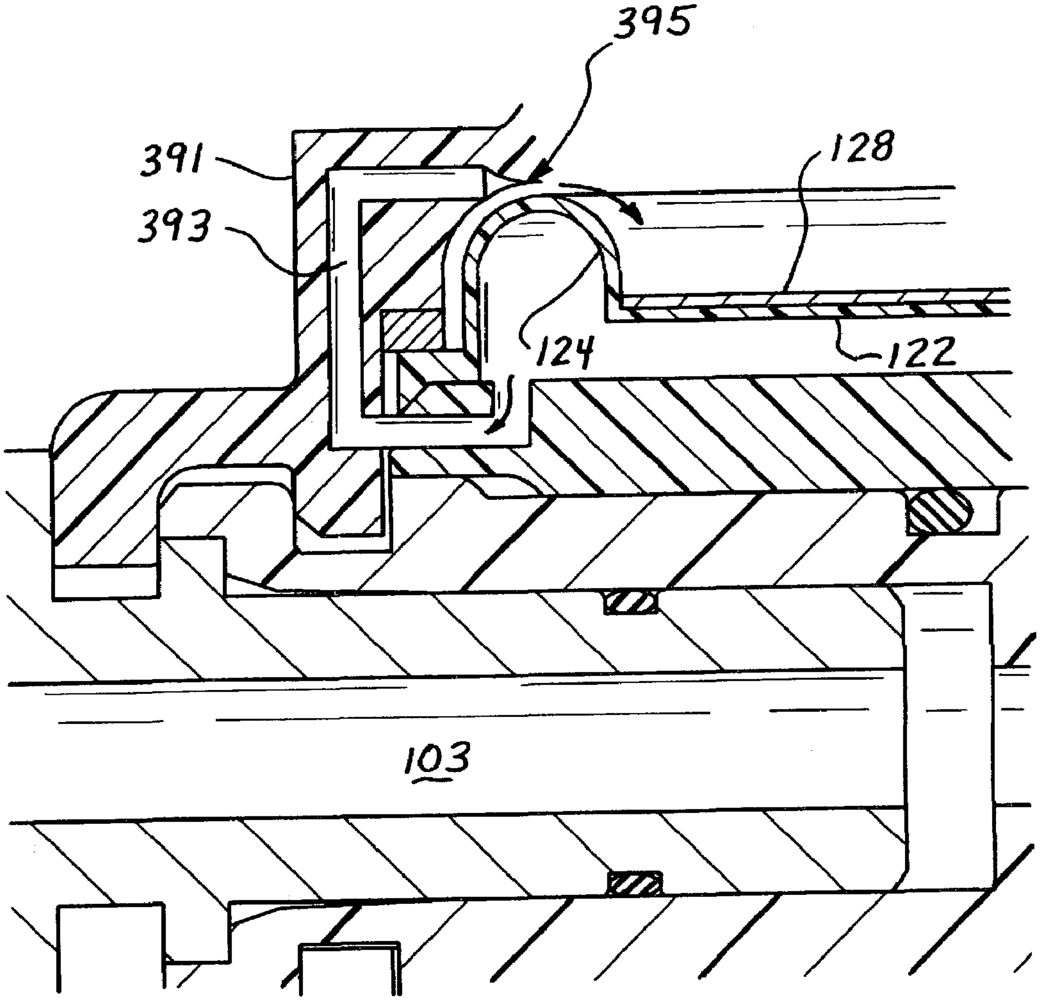
FIG. 10 shows a cross-section of an alternative purge gas delivery system.

Looking more particularly at FIG. 10, it can be seen that the diaphragm 122, plate, or reinforcing disc of plastic or metal 128, and conduit or passage 103 has been shown. The side wall of the regulator 391 has been shown with a passage 393 connected to the positive pressure below the diaphragm 122. In this manner, air in the direction of the arrows can pass through passage 393 and out onto or over the outside of the diaphragm 122.

In order to protect the interior of the regulator from foreign substances, a duck bill valve 395 is shown. The duck bill valve 395 allows flow in the direction of the arrows, but prevents flow in the reverse direction.

Thus a delivery of uncontaminated purge gas onto or over the outside surface of the diaphragm 122 can be effected through this system as with the other orifices 170 or conduits.

What is claimed is:

1. A self contained breathing apparatus (SCBA) having a demand regulator comprising:

a source of breathing gas;

a mask with a lens;

a demand regulator connected to said mask and said source of breathing gas;

a flexible member in said demand regulator that moves in response to pressure differentials, said flexible member being at least in part formed of an elastomer, said flexible member having an outside portion exposed to ambient with an opposite inside portion of said flexible member in fluid communication with a user;

a valve for introducing breathing gas through said regulator to said mask connected for movement in response to movement of said flexible member;

a passage for providing breathing gas over the outside of said flexible member, said passage being formed as an opening from the inside of said flexible member to the outside; and a cover overlying said passage which can be displaced upon breathing gas flowing through said passage.

2. The SCBA as claimed in claim 1 further comprising:

said cover is an elastomeric member; and, said flexible member is a diaphragm.

3. The SCBA as claimed in claim 1 further comprising:

said flexible member is at least in part a diaphragm; and, said regulator when in use maintains a pressure above ambient in said mask and on the inside of said diaphragm.

4. The SCBA as claimed in claim 3 further comprising:

said passage provides flow over the outside of said diaphragm when said regulator is in use; and, an outlet is connected to the outside of said diaphragm for allowing flow from said passage to the ambient.

5. The SCBA as claimed in claim 4 wherein:

said cover is at least in part a flexible disk like member over said passage that allows flow thereunder when breathing gas flow is provided through said passage.

6. A self contained breathing apparatus (SCBA) having a demand regulator comprising:

a source of breathing gas;

a mask with a lens;

a demand regulator connected to said mask and said source of breathing gas;

a flexible member in said demand regulator that moves in response to pressure differentials, said flexible member being at least in part formed of an elastomer and being at least in part a diaphragm, said flexible member having an outside portion exposed to ambient with the opposite inside portion of said flexible member in fluid communication with a user;

a valve for introducing breathing gas through said regulator to said mask connected for movement in response to movement of said flexible member;

a passage for providing breathing gas over the outside of said flexible member, said passage being formed as an opening from the inside of said flexible member to the outside, said passage providing flow over the outside of said diaphragm when said regulator is in use;

said regulator when in use maintaining a pressure above ambient in said mask and on the inside of said diaphragm;

an outlet is connected to the outside of said diaphragm for allowing flow from said passage to the ambient; and, a flexible disk like member over said passage that allows flow thereunder when breathing gas flow is provided through said passage.

7. The SCBA as claimed in claim 6, wherein:

at least a portion of said flexible disk like member can be displaced upon breathing gas flowing through said passage.

8. The SCBA as claimed in claim 7 further comprising:

said flexible disk like member is an elastomeric member; and, said flexible member is a diaphragm.

9. A demand breathing gas regulator comprising:

a regulator body for fluid connection to a user's mask and a source of breathing gas;

a flexible member operably connected to a breathing gas demand valve supported by said regulator body, said flexible member being at least in part formed of a diaphragm, said flexible member having one side exposed to ambient through an opening in said regulator;

a passage for delivery of breathing gas over a face of said flexible member exposed to ambient, said passage being formed through said flexible member; and, a cover overlying said passage which moves in response to breathing gas flowing through said passage.

10. A self contained breathing apparatus (SCBA) comprising:

a tank for containment of breathing gas;

a first stage regulator fluidically connected to said tank;

a second stage regulator fluidically connected to said first stage regulator;

a mask fluidically connected to said second stage regulator;

a diaphragm in said second stage regulator having an outside portion exposed to ambient with the opposite inside portion of said diaphragm in fluid communication with a user;

a pilot valve fluidically connected to a second valve for causing flaw of breathing gas, said pilot valve being located on the inside of said regulator for providing breathing gas at a pressure above ambient; and a passage through said diaphragm from the inside portion thereof to provide breathing gas on the outside of said diaphragm.

11. A self contained breathing apparatus (SCBA) comprising:

a tank for containment of breathing gas;

a first stage regulator fluidically connected to said tank;

a second stage regulator fluidically connected to said first stage regulator;

a mask fluidically connected to said second stage regulator;

a diaphragm in said second stage regulator having an outside portion exposed to ambient with an opposite inside portion of said diaphragm in fluid communication with a user;

a valve operably connected to the diaphragm on an inside of said second stage regulator for providing breathing gas at a pressure above ambient;

a passage through said diaphragm from the inside portion thereof to provide breathing gas on the outside portion of said diaphragm; and a cover overlying said passage which allows flow from said passage when breathing gas flows therethrough.

12. The SCBA as claimed in claim 11, wherein: said diaphragm and said cover are comprised at least in part of an elastomeric material.

13. A method for providing regulated breathing gas through a demand regulator comprising:

providing a source of breathing gas;

regulating said breathing gas to an intermediate pressure by a first stage regulator;

conducting said intermediate pressure gas to a demand regulator;

regulating said intermediate pressure by a demand regulator having a flexible member exposed on one side to ambient and on an opposite side to breathing gas, said intermediate pressure being regulated by a valve mechanism connected to said flexible member, passing said breathing gas over the one side of said flexible member exposed to ambient;

allowing said breathing gas to flow from the opposite side of said flexible member to the side exposed to ambient; and covering said flexible member at least in part when breathing gas is not passing to the side exposed to ambient.

14. The method as claimed in claim 13 further comprising:

said flexible member is formed at least in part from an elastomer.

15. A method of purging ambient contaminants from a demand breathing gas regulator comprising:

providing a demand regulator served by a source of breathing gas, said demand regulator having a flexible member exposed on one side to ambient conditions and on an opposite side to the breathing gas, said flexible member being at least in part an elastomeric diaphragm;

passing breathing gas to the side of said flexible member exposed to ambient and purging at least in part any contaminants from said flexible member by the flow of said gas, said breathing gas being passed through an opening of said diaphragm; and, covering said opening when breathing gas is not passing therethrough.

16. The method as claimed in claim 15 wherein:

said diaphragm is covered by a disc.

17. A demand breathing gas regulator comprising:

a regulator body for fluid connection to a user's mask and a source of breathing gas;

a flexible member operably connected to a breathing gas demand valve supported by said regulator body, said flexible member having one side exposed to ambient through an opening in said regulator;

a passage for delivery of breathing gas over a face of said flexible member exposed to ambient;

a cover overlying said passage, at least a portion of said cover being displaced upon flow of breathing gas through said passage;

a pilot valve of said regulator that moves in response to pressure differentials on said flexible member; and, a second valve which valves breathing gas through said regulator in response to said pilot valve.

* * * * *

UNITED STATES PATENT AND TRADEMARK OFFICE

CERTIFICATE OF CORRECTION

PATENT NO. : 6,966,316 B2 Page 1 of 1

APPLICATION NO. : 10/322833

DATED : November 22, 2005

INVENTOR(S) : Philip L. Lowry

It is certified that error appears in the above-identified patent and that said Letters Patent is hereby corrected as shown below:

In Column 4, Line 35, after "mask" insert --22.--,

In Column 5, Line 44, (Approx.), delete "driver" and insert --driven--, therefore.

In Column 8, Line 26 (Approx.), Claim 1, after "and" insert --,--.

In Column 9, Line 43, Claim 10, delete "flaw" and insert --flow--, therefore.

In Column 10, Line 17, Claim 13, delete "member," and insert --member;--, therefore.

Signed and Sealed this

Twelfth Day of December, 2006

JON W. DUDAS

*Director of the United States Patent and Trademark Office*